United States Patent [19]
Dooms et al.

[11] Patent Number: 5,789,021
[45] Date of Patent: Aug. 4, 1998

[54] LUMINESCENT ARTICLE WITH HIGH PIGMENT TO BINDER RATIO AND MANUFACTURE THEREOF

[75] Inventors: Philip Dooms, Edegem; Jozef Aertbelien, Schilde; Jan Van Havenbergh, Zwijndrecht, all of Belgium

[73] Assignee: AGFA-Gevaert, N.V., Mortsel, Belgium

[21] Appl. No.: 331,577

[22] PCT Filed: Jun. 17, 1993

[86] PCT No.: PCT/EP93/01552

§ 371 Date: Nov. 2, 1994

§ 102(e) Date: Nov. 2, 1994

[87] PCT Pub. No.: WO94/00531

PCT Pub. Date: Jan. 6, 1994

[30] Foreign Application Priority Data

Jun. 23, 1992 [EP] European Pat. Off. .............. 92201840

[51] Int. Cl.$^6$ .................................................. B05D 5/12
[52] U.S. Cl. .................. 427/64; 250/483.1; 250/484.4; 427/66; 427/203; 427/204; 427/205
[58] Field of Search ................ 250/483.1, 484.4; 427/64, 66, 203, 204, 205

[56] References Cited

U.S. PATENT DOCUMENTS

| | | | |
|---|---|---|---|
| 4,574,102 | 3/1986 | Arakawa et al. | 250/483.1 |
| 4,645,721 | 2/1987 | Arakawa et al. | 250/483.1 |
| 4,791,009 | 12/1988 | Arakawa et al. | 427/64 |
| 4,855,191 | 8/1989 | Arakawa et al. | 250/483.1 |
| 5,032,732 | 7/1991 | Ito | 250/484.1 |

FOREIGN PATENT DOCUMENTS

| | | |
|---|---|---|
| 0 209 358 | 1/1987 | European Pat. Off. . |
| 0 393 662 | 10/1990 | European Pat. Off. . |
| 0393662A3 | 10/1990 | European Pat. Off. . |
| 0 503 702 | 9/1992 | European Pat. Off. . |
| 2 146 271 | 3/1973 | France . |

*Primary Examiner*—Michael Lusignan
*Attorney, Agent, or Firm*—Breiner & Breiner

[57] ABSTRACT

In accordance with the present invention a luminescent article is provided which luminescent article comprises a self-supporting or supported layer of phosphor particles dispersed in a binding medium and a protective coating thereover characterised in that the binding medium comprises one or more rubbery and/or elastomeric polymers, in that the ratio by volume of pigment to binding medium is at least 70:30 and at most 92:8 and the packing ratio is less than 67%. By said rubbery and/or elastomeric polymers the phosphor layer has improved elasticity of the screen, high protection against mechanical damage and thus high ease of manipulation and high pigment to binder ratio. Moreover no compression manipulation is necessary to get a thinner coated phosphor layer with reduced voids, and nevertheless a better image quality, i.a. sharpness, is obtained. One or more antioxidants may be present.

12 Claims, No Drawings

LUMINESCENT ARTICLE WITH HIGH PIGMENT TO BINDER RATIO AND MANUFACTURE THEREOF

FIELD OF THE INVENTION

The present invention relates to radiation-sensitive luminescent articles comprising a coated layer of phosphor particles in a binder and to a method to manufacture the said articles.

BACKGROUND OF THE INVENTION

In radiography the interior of objects is reproduced by means of penetrating radiation which is high energy radiation belonging to the class of X-rays, γ-rays and high energy elementary particle radiation, e.g. β-rays, electron beam or neutron radiation. For the conversion of penetrating radiation into visible light and/or ultraviolet radiation luminescent substances are used called phosphors.

In a conventional radiographic system an X-ray radiograph is obtained by X-rays transmitted imagewise through an object and converted into light of corresponding intensity in a so-called intensifying screen (X-ray conversion screen) wherein phosphor particles absorb the transmitted X-rays and convert them into visible light and/or ultraviolet radiation whereto a photographic film is more sensitive than to the direct impact of the X-rays.

In practice the light emitted imagewise by said screen irradiates a contacting photographic silver halide emulsion layer film which after exposure is developed to form therein a silver image in conformity with the X-ray image.

For use in common medical radiography the X-ray film comprises a transparant film support double-side coated with a silver halide emulsion layer. During the X-ray irradiation said film is arranged in a cassette between two X-ray conversion screens each of them making contact with their corresponding silver halide emulsion layer.

Single side coated silver halide emulsion films combined in contact with only one screen are often used in autoradiography, in applications where improved image definition is of great importance e.g. in mammography and in particular fields of non-destructive testing (NDT) known as industrial radiography. An autoradiograph is a photographic record formed through the intermediary of penetrating radiation emitted by radioactive material contained in an object, e.g. microtome cut for biochemical research.

Phosphors suitable for use in the conventional radiographic system must have a high prompt emission on X-ray irradiation and low after-glow in favour of image-sharpness.

More recently an X-ray recording system has been developed wherein photostimulable storage phosphors are used that in addition to their immediate light emission (prompt emission) on X-ray irradiation, have the property to store temporarily a large part of the energy of the X-ray image which energy is set free by photostimulation in the form of light different in wavelength characteristic from the light used in the photostimulation. In said X-ray recording system the light emitted on photostimulation is detected photoelectronically and transformed in sequential electrical-signals.

The basic constituents of such X-ray imaging system operating with storage phosphors are an imaging sensor containing said phosphor, normally a plate or panel, which temporarily stores the X-ray energy pattern, a scanning laser beam for photostimulation, a photo-electronic light detector providing analog signals that are converted subsequently into digital time-series signals, normally a digital image processor which manipulates the image digitally, a signal recorder, e.g. magnetic disk or tape, and an image recorder for modulated light-exposure of a photographic film or an electronic signal display unit, e.g. cathode ray tube.

From the preceding description of said two X-ray recording systems operating with X-ray conversion phosphor screens in the form of a plate or panel it is clear that said plates or panels serve only as intermediate imaging elements and do not form the final record. The final image is made or reproduced on a separate recording medium or display. The phosphor plates or sheets can be repeatedly re-used. Before re-use of the photostimulable phosphor panels or sheets a residual energy pattern is erased by flooding with light. The expected life of the plate is limited mainly by mechanical damage such as scratches.

Both types of X-ray conversion screens generally comprise in order : a support, a layer comprising phosphor particles dispersed in a suitable binder and a protective coating coated over the phosphor containing layer to protect said layer during use.

Since in the above described X-ray recording systems the X-ray conversion screens are used repeatedly, it is important to provide them with an adequate topcoat for protecting the phosphor containing layer from mechanical and chemical damage. Therefore the protective layer preferably has a relief structure that reduces friction as well as the tendency to show sticking phenomena with contacting materials, thus favouring loading and unloading of a film from a cassette and reducing the building up of static electricity.

Once the cassette has been loaded the contact between the film and the conventional screens, which depends on the contact area and the distance between both the screens and the photographic film, is important to obtain good image quality. The optimization of the relationship between image quality and the physical characteristics of the topcoat layer of the screens has been disclosed in EP-Application No. 510 754.

From the point of view of the phosphor layer especially an increased thickness itself can give rise to increased unsharpness of the emitted light, this being the more unfavourable if the weight ratio between the amount of phosphor particles and the amount of binder decreases for the same coating amount of said phosphor particles, also called "pigment".

Enhancing the weight ratio amount of pigment to binder to provide sharper images, by decreasing the amount of binder leads to unacceptable manipulation characteristics of the screen due to e.g. insufficient elasticity and brittleness of the coated phosphor layer in the screen.

One way to get thinner coated phosphor layers without changing the coated amounts of pigment and of binder makes use of a method of compressing the coated layer containing both ingredients at a temperature not lower than the softening point or melting point of the thermoplastic elastomer as has been described in EP-Application 393 662. By this method the void ratio becomes remarkably reduced. Screens manufactured in this way are characterised by a packing ratio of the phosphor in the phosphor layer, defined as in EP-Application 393 662 p. 12, formulae (I) and (II), of not less than 70% due to this compression and—in order to avoid destruction of the phosphor by compression—by the use of from 10 to 100% by weight of thermoplastic binder based on the total amount of binder.

OBJECTS OF THE INVENTION

It is an object of the present invention to provide a luminescent article, e.g. in the form of a plate, panel or web, comprising a phosphor-binder layer and a protective coating applied thereto, the phosphor layer having a ratio by volume of pigment to binder to obtain an excellent image resolution with the maintenance of a high ease of manipulation, thereby providing a good elasticity of the screen, good adhesion properties between the support and the phosphor layer and avoiding brittleness of the said phosphor layer.

Other objects and advantages of the invention will become clear from the following description and examples.

SUMMARY OF THE INVENTION

In accordance with the present invention a luminescent article is provided which luminescent article comprises a self-supporting or supported layer of phosphor particles dispersed in a binding medium and a protective coating thereover characterised in that the binding medium substantially consists of one or more rubbery and/or elastomeric polymers, in that the ratio by volume of phosphor to binding medium is at least 70:30 and at most 92:8 and in that the packing ratio is less than 67%.

By the choice of the type of binder and the high volume ratio of phosphor to binder it is possible to obtain thin phosphor coatings offering not only high resolution but also high sensitivity without the need for increasing the packing density by compressing so as to reduce the voids as defined in EP-A 393 662 to a value of not less than 70%. Moreover the phosphor layer retains high protection against mechanical damage and thus high ease of manipulation.

The present invention further provides a method of producing a luminescent article as defined by the steps of dispersing phosphor particles in a binding medium substantially consisting of one or more rubbery and/or elastomeric polymers, coating said dispersed phosphor particles so as to form a phosphor layer without compressing the said dried phosphor layer and coating a protective coating layer thereover.

DETAILED DESCRIPTION OF THE INVENTION

As elastomeric binders natural and synthetic rubbers can be used as e.g. diene rubbers, butadiene, isoprene, styrene, styrene-butadiene, polychloroprene, silicone, urethane, butyl, acrylic and nitrile rubbers, vinylpyridine rubbers, polysulphide rubbers, epichloorhydrine rubbers and the like as e.g. those mentioned in EP-Specifications Nos. 102 085 and 113 656.

Particularly preferred elastomers are thermoplastic rubbers and still more preferred are thermoplastic block copolymers with elastomeric or rubbery properties. Typical examples of this class are block-copolymers (di-block, tri-block, star-block etc.-copolymers) of the styrene-diene type. Preferred rubbery block-copolymers in accordance with this invention are styrene-butadiene, styrene-isoprene, styrene-butadiene-styrene, styrene-isoprene-styrene etc. rubbers which allow the pigment to binder volume ratio amount to be enhanced to more than 70/30 and more preferably to at least 85/15 with preservation of the elasticity of the screen, avoiding brittleness, and providing an enhanced sharpness and sensitivity. The volume ratio is the more preferred term in this application as it is independant on the densities, and consequently also independant on the weight of phosphor and binder.

Moreover in accordance with this invention the packing ratio of the phosphor in the phosphor layer is less than 67%. The said packing ratio can be calculated by the formula (III) given in EP-Application 393 662, p. 12, wherein the density of the phosphor has to be inserted.

Well-known trade-mark names for said block-copolymer rubbers are CARIFLEX, KRATON, SOLPRENE, TUFPRENE, EUROPRENE, BUNA BL, etc..

Originally the term "rubber" was referring to the hydrocarbon polymer having isoprene units in its structure obtained from the rubber tree. With the development of synthetic rubbers having some rubbery characteristics, differing in chemical structure as well as properties, a more general designation was needed to cover both "natural" and "synthetic rubbers".

The term "elastomer", a contraction of the words "elastic" and "polymer" was introduced, and defined as a substance that can be stretched at room temperature to at least twice its original length and, after having been stretched and the stress removed, returns with force to approximately its original length in a short time.

Requirements to be met for rubbery properties to be present in both natural and synthetic rubbers are: the presence of long thread-like molecules, flexibility in the molecular chain to allow flexing and coiling, and some mechanical and chemical bonds between molecules. Most of the synthetic rubbers are also commercially available in the form of a latex, being a colloidal suspension of polymers in an aqueous medium or in the form of solid flakes, being soluble in organic solvents.

Styrene-butadiene rubber is the most important synthetic rubber and the most widely used rubber in the entire world. Styrene has an ethylenic linkage in its structure which readily undergoes addition reactions with suitable co-monomers as e.g. the conjugated diolefin butadiene, under the influence of heat, light or catalysts, to copolymerize, yielding elastomers or synthetic rubbers as block-copolymers.

Isoprene is well-known as a five-carbon, conjugated diolefin or diene, exhibiting all the characteristic reactions of dienes, like e.g. butadiene, and can be obtained by the destructive destination of gas oil, naphthas, rubber etc., polymerizing readily to form dimers and high-molecular-weight resins.

The present invention uses the above types of natural and synthetic rubbers as binder for the phosphor particles.

Particularly suitable thermoplastic rubbers, used as binders in phosphor screens in accordance with this invention are the three block-copolymers of SHELL being available as CARIFLEX Thermoplastic Rubbers "Cariflex SBR", "Cariflex IR" and "Cariflex BR", referring to styrene-butadiene rubber, isoprene rubber and butadiene rubber respectively, CARIFLEX being a trade mark name from SHELL.

In comparison with other well-known binders as disclosed e.g. in U.S. Pat. Nos. 2,502,529; 2,887,379; 3,617,285; 3,043,710; 3,300,310; 3,300,311 and 3,743,833 the pigment to binder volume ratio can be remarkably increased to the preferred values set forth hereinbefore. For the hitherto used binders this ratio was clearly limited by the lack in physical properties of the coated phosphor layers.

An increase in the volume ratio of phosphor to binder providing a reduction of the thickness of the coating layer for an equal phosphor coverage not only gives a better sharpness but, unexpectedly, also a higher sensitivity.

It should be stressed that the better sharpness is obtained without making use of mechanical compression of the coated phosphor layer. Within the scope of this invention a reduction of the void ratio of the phosphor layer is not required. Said void ratio is expressed in EP-Application 393 662, formulae (I) and (II) p. 12. A reduction of its value is a necessary feature in the said EP-Application as a reduction of the layer thickness is required to enhance the sharpness: rubbery binders make compression possible. Otherwise in our invention rubbery binders are chosen because they allow a high volume ratio of pigment to binder, resulting in excellent physical properties and image quality and rather unexpectedly in an enhanced sensitivity.

The small amount of binding agent does not result in too brittle a layer and the phosphor layer should contain sufficient binder, only to give structural coherence to the layer. This can be translated as promoting the "elasticity" and "brittleness" of the screen. Especially for storage phosphor members this factor is very important in view of the manipulations said member is exposed to. In this connection a volume ratio of phosphor to binder higher than 92/8 is hardly allowable.

A mixture of one or more thermoplastic rubber binders may be used in the coated phosphor layer(s).

As antioxidants, preventing yellowing of the rubbery binder that may still occur after a long period of time, use can be made of the following products without however being limited thereto: Irganox 1010, trademarked product from CIBA-GEIGY; Antioxidant 330, trademarked product from ETHYL CORP.; Antioxidant 2246 and 425, trademarked products from AMERICAN CYANAMID; Vanox 2246, trademarked product from R. T. VANDERBILT; Santowhite Crystals, trademarked product from MONSANTO Co.; Polyguard, trademarked product from UNIROYAL CHEM. Co. and Weston 618, trademarked product from BORG-WARNER.

Luminescent articles as described hereinbefore, according to this invention, may be provided with at least one of the said antioxidants. The antioxidants are preferably incorporated in the phosphor layer.

As is well-known the sensitivity of the screen is determined by the chemical composition of the phosphor, its crystal structure and crystal size properties and the weight amount of phoshor coated in the phosphor layer. The image quality, particularly sharpness, especially depends on optical scattering phenomena in the phosphor layer being determined mainly by the thickness of the phosphor layer and the packing density. Said packing density of the phosphor particles depends on the crystal size distribution of the phosphor particles, their morphology and the amount of binder present in the phosphor layer or layers. In accordance with the present invention the rubbery medium makes high ratio by volume of phosphor to binding medium possible without the need for compression so that the packing ratio remains less than 67% when defined according to the corresponding the formula of EP 393 662, p. 12, to calculate the said packing ratio.

Another factor determining the sensitivity of the screen is the thickness of the phosphor layer. Said thickness may be within the range of from 10 to 1000 μm, preferably from 50 to 500 μm and more preferably from 100 to 300 μm.

The coverage of the phosphor or phosphors present as a sole phosphor or as a mixture of phosphors whether or not differing in chemical composition and present in one or more phosphor layer(s) in a screen is preferably in the range from about 300 to 1500 g/m$^2$. Said one or more phosphor layers may have the same or a different layer thickness and/or a different weight ratio amount of pigment to binder and/or a different phosphor particle size or particle size distribution. It is general knowledge that sharper images with less noise are obtained with phosphor particles of smaller mean particle size, but light emission efficiency declines with decreasing particle size. Thus, the optimum mean particle size for a given application is a compromise between imaging speed and image sharpness desired. Preferred average grain sizes of the phosphor particles are in the range of 2 to 30 μm and more preferably in the range of 2 to 20 μm.

In the phosphor layer(s), any phosphor or phosphor mixture may be coated depending on the objectives that have to be attained with the manufactured intensifying or storage phosphor screens. It is possible to mix fine grain phosphors with more coarse grain phosphors to increase the packing density.

Preferred phosphors are e.g. yttriumtantalate phosphors, the preparation of which is described in EP-Specifications 011 909 and 202 875 and in U.S. Pat. No. 5,064,729 or barium fluorobromide phosphors the preparation of which proceeds analogously to the preparation of barium fluorochloride phosphors described e.g. in GB-Patent 1,161,871 and 1,254,271 and in U.S. Pat. No. 4,088,894. A preferred barium fluorobromide phosphor has the following empirical formula: $BaFBr:Eu_{0.05}$, the preparation of said phosphor being carried out in such a way that at least part of the europium-activator is in the trivalent state so that the phosphor has a high prompt emission on X-ray exposure as described e.g. in Radiology 148, p. 833–838, September 1983.

Both cited prompt emission phosphors are emitting in the near UV and blue region of the visible spectrum, i.e. mainly in a wavelength range of 360 to 450 nm, and as such can be used in conjunction with a photographic silver halide emulsion film having inherent sensitivity in that spectrum range, e.g. a duplitized silver halide emulsion layer film of the type described in GB-P 1,477,637 which has to be read therefor in conjunction herewith. Said phosphors can be coated individually into one or more phosphor layers of a screen in accordance with this invention or a phosphor composition may be made of a mixture of both phosphors in a weight ratio range of 80/20 to 20/80 as described in EP-Application 435 241. By the use of a mixture it is possible to produce X-ray conversion screens that have a higher brightness than phosphor screens containing solely the tantalate phosphor, resulting in the receipt of a lower X-ray dose for the patient in medical diagnosis. An extra improvement in image-sharpness can be realized with the thermoplastic rubber binders cited hereinbefore when using said phosphor mixture because thinner phosphor layers are possible at higher phosphor to binder ratio.

It is clear that within the scope of this invention the choice of the phosphor or phosphor mixture is not limited to the preferred phosphors cited hereinbefore.

In radiation image storage panels according to this invention e.g. divalent europium-doped bariumfluorohalide phosphors may be used, wherein the halide-containing portion may be (1) stoichiometrically equivalent with the fluorine portion as e.g. in the phosphor described in claim 1 of U.S. Pat. No. 4,239,968, (2) may be substoichiometrically present with respect to the fluorine portion as described e.g. in EP-Application 0 021 342 or 0 345 904 and U.S. Pat. No. 4,587,036, or (3) may be superstoichiometrically present with respect to the fluorine portion as described e.g. in claim 1 of U.S. Pat. No. 4,535,237.

Divalent europium activated barium fluorobromide phosphors suitable for use according to the present invention have been described in EP-Application No. 533 236 and in the corresponding U.S. Ser. No. 07/941,167.

Still other divalent europium activated barium fluorobromide phosphors suitable for use according to the present invention have been described in EP-Application No. 533 234 and in the corresponding U.S. Ser. No. 07/935,291.

Particularly suitable divalent europium barium fluorobromide phosphors for use according to that invention correspond to the empirical formula (I) of EP-Application No. 533 236 and contain in addition to the main dopant $Eu^{2+}$ at least one alkali metal, preferably sodium or rubidium, as co-dopant.

Other particularly suitable barium fluorobromide phosphors for use according to the present invention contain in addition to the main dopant $Eu^{2+}$ at least Sm as codopant as described in EP-Application No. 533 233 and in the corresponding U.S. Ser. No. 07/940,985.

A radiographic screen according to the present invention can be prepared by the following manufacturing process. The phosphor layer can be applied to the support by any coating procedure, making use of solvents for the binder of the phosphor containing layer as well as of useful dispersing agents, useful plasticizers, useful fillers and subbing or interlayer layer compositions that have been described in extenso in the European Patent Application No. 510 753 and in the corresponding U.S. Ser. No. 07/871,328.

In accordance with this invention phosphor particles are mixed with dissolved rubbery and/or elastomeric polymers, in a suitable mixing ratio to prepare a dispersion. Said dispersion is uniformly applied to a substrate by a known coating technique, e.g. doctor blade coating, roll coating, gravure coating or wire bar coating, and dried to form a luminescent layer fluorescing by X-ray irradiation and called hereinafter fluorescent layer. Further mechanical treatments like compression to lower the void ratio is not required within the scope of this invention.

Useful dispersing agents to improve the dispersibility of the phosphor particles dispersed into the coating dispersion are described in EP-Application No. 510 753 and in the corresponding U.S. Ser. No. 07/871,328 as well as a variety of additives that can be added to the phosphor layers such as a plasticizer for increasing the bonding between the binder and the phosphor particles in the phosphor layer and a light-reflecting or absorbing filler and/or a colorant.

Examples of preferably used solvents, also with a view to phosphor recovery purposes from worn-out screens, requiring the phosphor containing layer to be soluble and to remain soluble after coating, include lower alcohols such as methanol, ethanol, n-propanol and n-butanol; chlorinated hydrocarbons such as methylene chloride and ethylene chloride; ketones such as acetone, butanone, methyl ethyl ketone and methyl isobutyl ketone; esters of lower alcohols with lower aliphatic acids such as methyl acetate, ethyl acetate and butyl acetate; ethers such as dioxane, ethylene glycol monoethylether; methyl glycol; and mixtures of the above-mentioned solvents. Particularly preferred in combination with ethyl acetate as a preferred ester is toluene as an aromatic solvent used to solve the thermoplastic rubbers, present as solid flakes.

Examples of useful dispersing agent include ionic and nonionic dispersing agents or combinations thereof, well-known for that purpose e.g., GAFAC RM 710 (tradename) a polyoxyethylene (20) sorbitan monopalmitate and monolaurate marketed by General Aniline and Film Company (GAF), New York, USA, polymeric surfactants such as the acrylic graft copolymer, PHOSPHOLIPON 90 (tradename) marketed by Nattermann-Phospholipid GmbH, Köln, W. Germany, silane dispersing agents and surfactants e.g. DOW CORNING 190 (tradename) and SILANE Z6040 (tradename) marketed by Dow Corning Corporation, Midland, Mich., USA or glymo 3-glycidyloxypropylmethoxysilane or organosulfate polysilanes, unsaturated p-aminamide salts and high molecular acid esters such as ANTI TERRA U 80 (tradename) marketed by BYK-Chemie GmbH, Wesel, W. Germany, high molecular unsaturated polyesters. Dispersing agents are added in an amount of 0.05 to 10% by weight as compared to the phosphor.

Useful plasticizers include phosphates such as triphenyl phosphate, tricresyl phosphate and diphenyl phosphate; phthalates such as diethyl phthalate and dimethoxyethyl phthalate; glycolates such as ethylphthalyl ethyl glycolate and butylphthalyl butyl glycolate; polymeric plastizers, e.g. and polyesters of polyethylene glycols with aliphatic dicarboxylic acids such as polyester of triethylene glycol with adipic acid and polyester of diethylene glycol with succinic acid.

The coating dispersion may contain a filler (reflecting or absorbing) or may be colored by a colorant capable of absorbing light within the spectrum emitted by the phosphor or capable of absorbing excitation light in the case of a stimulable X-ray conversion screen. Examples of colorants include Solvent Orange 71 (Diaresin Red 7), Solvent Violet 32 (Diaresin Violet A), Solvent Yellow 103 (Diaresin Yellow C) and Solvent Green 20 (all four supplied by Mitsubishi Chemical Industries, Japan), Makrolex Rot GS, Makrolex Rot EG, Makrolex Rot E2G, Helioechtgelb 4G and Helioechtgelb HRN (all five marketed by Bayer, Leverkusen, Germany), Neozaponfeuerrot G and Zaponechtbraun BE (both marketed by BASF, Ludwigshafen, W. Germany).

In the preparation of a radiographic screen, one or more additional layers are occasionally provided between the support and the phosphor containing layer, having subbing or interlayer layer compositions, so as to improve the bonding between the support and the phosphor layer, or to improve the sensitivity of the screen or the sharpness and resolution of an image provided thereby. For instance, a subbing layer or an adhesive layer may be provided by coating polymer material such as gelatin over the surface of the support on the phosphor layer side. A light-reflecting layer may be provided, e.g. by vacuum-depositing an aluminium layer or by coating a pigment-binder layer wherein the pigment is e.g. titanium dioxide. For the manufacture of light-absorbing layer, serving as anti-halation layer, carbon black dispersed in a binder may be used but also any known anti-halation dye. Such additional layer(s) may be coated on the support either as a backing layer or interposed between the support and the phosphor containing layer(s) Several of said additional layers may be applied in combination.

Radiographic screens, in particular those comprising conventional non-stimulable phosphors, can also be made in the form of gradual screens, i.e. screens having a gradual intensification along their length and/or width. Graduality can be achieved by gradually increasing the thickness of the phosphor layer over the length or width of the screen or by incorporating into the protective layer or into an interlayer between the protective layer and phosphor containing layer a gradually increasing amount of dye capable of absorbing the light emitted by the phosphor.

According to another convenient technique graduality is obtained by halftone printing of a dye or ink composition absorbing the light emitted by the screen. By varying the screen dot size in the halftone print, i.e. by gradually varying the percent dot area over the length or width of the screen graduality can be obtained in any degree. The halftone printing can proceed on the phosphor containing layer which thereupon is covered with the protective coating or proceeds by applying the protective coating by halftone printing, e.g. by gravure roller or silk screen printing.

In the preparation of the phosphor screen having a primer layer between the substrate and the fluorescent layer, the primer layer is provided on the substrate beforehand, and then the phosphor dispersion is applied to the primer layer and dried to form the fluorescent layer.

After applying the coating dispersion onto the support, the coating dispersion is heated slowly to dryness so as to complete the formation of a phosphor layer. In order to remove as much as possible entrapped air in the phosphor coating composition it can be subjected to an ultra-sonic treatment before coating.

After the formation of the fluorescent layer, a protective layer is generally provided on top of the fluorescent layer. The roughness of the topcoat layer of especially the intensifying screens offers the advantage that sticking phenomena between a film and an intensifying screen(s) in a cassette are substantially avoided even after intimate contact due to pressure build-up in the cassette system.

Correlating features of roughness and thickness of the protective coating conferring to the screens of the present invention desirable and unexpected properties of ease of manipulation and excellent image sharpness have been described in the EP-Application No. 510 754.

In relation to transport characteristics of a film in a cassette the use of an X-ray conversion phosphor screen having a topcoat with embossed structure favours its practically frictionless loading and unloading of a cassette and reduces considerably the built up of static electricity. The micro-channels formed by the embossed structure of the protective coating allow air to escape between phosphor screen and contacting film whereby image quality (image sharpness) is improved by better screen-film-screen contact without large air bubble inclusions.

According to a preferred embodiment the coating of the protective layer here proceeds by screen-printing (silk-screen printing).

In a preferred embodiment the protective coating composition is applied by a rotary screen printing device as has been described in detail in EP-Application No. 510 753.

Very useful radiation curable compositions for forming a protective coating contain as primary components
(1) a crosslinkable prepolymer or oligomer,
(2) a reactive diluent monomer, and in the case of an UV curable formulation
(3) a photoinitiator.

Examples of suitable prepolymers for use in a radiation-curable composition applied according to the present invention are the following: unsaturated polyesters, e.g. polyester acrylates; urethane modified unsaturated polyesters, e.g. urethane-polyester acrylates. Liquid polyesters having an acrylic group as a terminal group, e.g. saturated copolyesters which have been provided with acryltype end groups are described in published EP-A 207 257 and Radiat. Phys. Chem., Vol. 33, No. 5, 443–450 (1989). The latter liquid copolyesters are substantially free from low molecular weight, unsaturated monomers and other volatile substances and are of very low toxicity (ref. the journal Adhasion 1990 Heft 12, page 12). The preparation of a large variety of radiation-curable acrylic polyesters is given in German Offenlegungsschrift No. 2838691. Mixtures of two or more of said prepolymers may be used. A survey of UV-curable coating compositions is given e.g. in the journal "Coating" 9/88, p. 348–353.

When the radiation-curing is carried out with ultraviolet radiation (UV), a photoinitiator is present in the coating composition to serve as a catalyst to initiate the polymerization of the monomers and their optional cross-linking with the pre-polymers resulting in curing of the coated protective layer composition. A photosensitizer for accelerating the effect of the photoinitiator may be present. Photoinitiators suitable for use in UV-curable coating compositions belong to the class of organic carbonyl compounds, for example, benzoin ether series compounds such as benzoin isopropyl, isobutylether; benzil ketal series compounds; ketoxime esters; benzophenone series compounds such as benzophenone, o-benzoylmethylbenzoate; acetophenone series compounds such as acetophenone, trichloroacetophenone, 1,1-dichloroacetophenone, 2,2-diethoxyacetophenone, 2,2-dimethoxy-2-phenylacetophenone; thioxanthone series compounds such as 2-chlorothioxanthone, 2-ethylthioxanthone; and compounds such as 2-hydroxy-2-methylpropiophenone, 2-hydroxy-4'-isopropyl-2-methylpropiophenone, 1-hydroxycyclohexylphenylketone; etc.

A particularly preferred photoinitiator is 2-hydroxy-2-methyl-1-phenyl-propan-1-one which product is marketed by E. Merck, Darmstadt, Germany under the tradename DAROCUR 1173. The above mentioned photopolymerization initiators may be used alone or as a mixture of two or more. Examples of suitable photosensitizers are particular aromatic amino compounds as described e.g. in GB-P 1,314, 556, 1,486,911, U.S. Pat. No. 4,255,513 and merocyanine and carbostyril compounds as described in U.S. Pat. No. 4,282,309.

To the radiation-curable coating composition there may be added a. storage stabilizer, a colorant, and other additives, and then dissolved or dispersed therein to prepare the coating liquid for the protective layer. Examples of colorants that can be used in the protective layer include MAKROLEX ROT EG, MAKROLEX ROT GS and MAKROLEX ROT E2G. MAKROLEX is a registered tradename of Bayer AG, Leverkusen, Germany.

When using ultraviolet radiation as curing source the photoinitiator which needs to be added to the coating solution will to a more or less extent also absorb the light emitted by the phosphor thereby impairing the sensitivity of the radiographic screen, particularly when a phosphor emitting UV or blue light is used. In case of use of a green emitting phosphor a photoinitiator has to be chosen of which the absorption range overlaps to a minimum degree with the emission range of the phosphor; a preferred photoinitiator is then DAROCUR 1173 (tradename).

The protective coating of the present luminescent article is given an embossed structure following the coating stage by passing the uncured or slightly cured coating through the nip of pressure rollers wherein the roller contacting said coating has a micro-relief structure, e.g. giving the coating an embossed structure so as to obtain relief parts. A suitable process for forming a textured structure in a plastic coating by means of engraved chill roll is described in U.S. Pat. No. 3,959,546.

According to another embodiment the textured or embossed structure is obtained already in the coating stage by applying the paste-like coating composition with a gravure roller or screen printing device operating with a radiation-curable liquid coating composition the Hoeppler-viscosity of which at a coating temperature of 25° C. is between 450 and 20,000 mPa.s.

To avoid flattening of the embossed structure under the influence of gravitation, viscosity and surface shear the radiation-curing is effected immediately or almost immediately after the application of the liquid coating. The rheologic behaviour or flow characteristics of the radiation-curable coating composition can be controlled by means of so-called flowing agents. For that purpose alkylacrylate ester copolymers containing lower alkyl (C1–C2) and higher alkyl (C6–C18) ester groups can be used as shear controlling agents lowering the viscosity. The addition of pigments such as colloidal silica raises the viscosity.

A variety of other optional compounds can be included in the radiation-curable coating composition of the present radiographic article such as compounds to reduce static electrical charge accumulation, plasticizers, matting agents, lubricants, defoamers and the like as has been described in EP-Application No. 510 753. In said document a description has also been given of the apparatus and methods for curing, as well as a non-limitative survey of X-ray conversion screen phosphors, of photostimulable phosphors and of binders of the phosphor containing layer.

The edges of the screen, being especially vulnerable by multiple manipulation, may be reinforced by covering the edges (side surfaces) with a polymer material being formed essentially from a moisture-hardened polymer composition prepared according to EP-Application No. 541 146 or the corresponding U.S. Ser. No. 7/963,999 by a process comprising the steps of :

(A) 30 to 99 parts by weight of at least one copolymer of olefinically unsaturated compounds having a weight-average molecular weight [Mw] of at least 1500 and containing chemically incorporated moieties capable of undergoing an addition reaction with amino groups, and (B) 1 to 70 parts by weight of organic substances containing blocked amino groups from which substances under the influence of moisture compounds having free primary and/or secondary amino groups are formed, wherein (i) the copolymers of component (A) contain intramolecularly bound carboxylic anhydride moieties, with the anhydride equivalent weight of the copolymers being from 393 to 9,800, and the binder composition contains from 0.25 to 10 anhydride moieties for each blocked amino group, II) coating the obtained mixture onto at least one side surface (edge) of said fluorescent screen, and (III) allowing moisture ($H_2O$) to come into contact with the coated mixture essentially consisting of the above defined components (A) and (B).

Support materials for radiographic screens in accordance with the present invention include cardboard, plastic films such as films of cellulose acetate, polyvinyl chloride, polyvinyl acetate, polyacrylonitrile, polystyrene, polyester, polyethylene terephthalate, polyamide, polyimide, cellulose triacetate and polycarbonate; metal sheets such as aluminum foil and aluminum alloy foil; ordinary papers; baryta paper; resin-coated papers; pigment papers containing titanium dioxide or the like; and papers sized with polyvinyl alcohol or the like. A plastic film is preferably employed as the support material.

The plastic film may contain a light-absorbing material such as carbon black, or may contain a light-reflecting material such as titanium dioxide or barium sulfate. The former is appropriate for preparing a high-resolution type radiographic screen, while the latter is appropriate for preparing a high-sensitivity type radiographic screen.

Examples of preferred supports include polyethylene terephthalate, clear or blue colored or black colored (e.g., LUMIRROR C, type X30 supplied by Toray Industries, Tokyo, Japan), polyethylene terephthalate filled with $TiO_2$ or with $BaSO_4$. Metals as e.g. aluminum, bismuth and the like may be deposited e.g. by vaporization techniques to get a polyester support having radiation-reflective properties.

These supports may have thicknesses which may differ depending on the material of the support, and may generally be between 60 and 1000 μm, more preferably between 80 and 500 μm from the standpoint of handling.

In common medical radiography the screens are fixed inside a cassette allowing the arrangement of a double-side coated silver halide emulsion film inbetween. In the radiographic exposure step one silver halide emulsion layer is exposed by the fluorescent light of a front screen (the screen most close to the X-ray source) and the other silver halide emulsion layer is exposed by the fluorescent light emitted by the back screen which is the screen struck by the X-rays that have penetrated already the photographic material.

Front and back screen may be asymmetrical in that e.g. their sensitometric properties, thickness, phosphor coverage and phosphor composition may be different.

Normally the screens described hereinbefore are applied for medical X-ray diagnostic applications but according to a particular embodiment the present radiographic screens may be used in non-destructive testing (NDT), of metal objects, where more energetic X-rays and γ-rays are used than in medical X-ray applications. In screens applied for industrial radiography it has been found advantageous to combine the fluorescent phosphor layer with a metal layer or metal support, wherein the metal has an atomic number in the range of 46 to 83 as described e.g. in U.S. Pat. Nos. 3,872,309 and 3,389,255. The metal layer in contact with the phosphor-containing layer acts as an emitter of photo-electrons and secondary X-rays when struck by highly energetic X-rays or gamma rays. The secondary lower energy X-rays and photo-electrons are absorbed in the adjacent phosphor-containing layer at a higher efficiency than the highly energetic X-rays and gamma rays emitted by an industrial X-ray apparatus, such results in an increase in photographic speed. Said metal layers or supports have the additional advantage of reducing the scattered radiation whereby image-sharpness is improved.

According to a particular embodiment described in Research Disclosure September 1979, item 18502 image-sharpness is improved by incorporating in the X-ray intensifying screen between the phosphor-containing layer and the support and/or at the rearside of the support a pigment-binder layer containing a non-fluorescent pigment being a metal compound, e.g. salt or oxide, of a heavy metal whose atomic number (Z) is at least 46. A preferred pigment used for that purpose is lead oxide (PbO) being applied e.g. at a coverage of 100 to 400 g of lead per $m^2$.

The invention is illustrated by the following examples without however limiting it thereto. All ratios are expressed by volume unless mentioned otherwise. Important physical properties as "adhesion" of the coated phosphor layer onto the support and "elasticity" or "brittleness" of the phosphor screens and properties concerning image quality as reflected in S-SWR measuring methods will be described hereinafter in the examples.

EXAMPLES

Definition of physical properties

Elasticity/brittleness

To describe the "elasticity" or "brittleness" of the screen, being two terms reflecting quite opposed properties, a qualitatively useful test has been developed.

A phosphor screen without protective layer having a phosphor coverage of 60 mg/cm² is bent around a pipe having a diameter of 1.5 cm.

If no damages in the form of small "cracks" are observed the elasticity of the screen is sufficiently good and is therefore given "A" as an evaluation mark, being equivalent to the absence of "brittleness".

If "cracks" are observed, the screen is too "brittle" and gets "B" as evaluation mark indicating a lack in elasticity.

Adhesion

Adhesion properties are obtained by the "cross-cut" test. With a knife, a wafer-like pattern is cut from the surface of the phosphor layer to such a depth as to reach the substrate layer. The wafer-like incisions are located at a distance of 0.5 cm and are crossing under an angle of 45°. A self-adhesive tape (TESA 4101) is sticked onto the wafer-like surface pattern and after stripping off the tape a qualitative evaluation is given. Obviously the test has to be carried out under reproducible circumstances as the pressure with which the tape is stuck onto the sample and the velocity and the way in which it is teared off. Three different marks may be obtained: "A" refers to perfect adhesion properties as no damages are observed, "B" refers to moderate adhesion properties and "C" to a bad quotation as the adhesion is quite insufficient.

Sensitometry for intensifying screens

X-ray exposure of "conventional" intensifying screens in combination with a radiographic film Pairs of screens of the same composition were arranged in the same type of cassette and between the screens and in contact therewith a same duplitized (double-side silver halide emulsion coated) film was inserted.

In manufacturing the film a silver bromoiodide emulsion (2 mole % of silver iodide) was used containing silver halide grains with an average grain size of 1.25 µm. The emulsion ready for coating contained per kg an amount of silver halide corresponding to 190 g of silver nitrate and 74 g of gelatin. As stabilizing agents the silver halide emulsion contained per kg 545 mg of 5-methyl-7-hydroxy-s-triazolo[1,5-a] pyrimidine and 6.5 mg of 1-phenyl-5-mercaptotetrazole.

The above emulsion was coated on both sides of a double side subbed polyethylene terephthalate support. To each of the dried silver halide emulsion layers a protective layer was applied containing 1.1 g/m² of gelatin, hardened with formaldehyd and containing perfluorocaprylic acid as an antistatic agent. The hardening proceeded by adding 0.03 grams of formaldehyde per gram of gelatin. Each silver halide emulsion layer contained an amount of silver halide equivalent with 7 g of silver nitrate per m².

The X-ray exposure proceeded according to ISO/DP9236 with 77 median kVp X-rays for chest exposure.

Processing of the exposed material

The processing of the thus exposed silver halide emulsion material proceeded with the following developing liquid, followed by fixing and rinsing at the indicated temperature and processing time.

Composition of the developing liquid (pH : 10.1)—(35° C., 27 s).

| Hydroquinone | 30 g/l |
|---|---|
| Potassium sulphite | 64 g/l |
| 1-Phenyl-3-pyrazolidinone | 1.5 g/l |
| Potassium bromide | 4 g/l |
| Glutardialdehyde | 4.7 g/l |

The pH was adjusted at 10.1 with bicarbonate/carbonate buffer.

Composition of the fixing liquid (pH : 4.3)—(34° C., 18 s).

| Ammonium thiosulphate | 132 g/l |
|---|---|
| Sodium sulphite | 10.8 g/l |
| Aluminium sulphate | 5.4 g/l |

The pH was adjusted at 4.3 with acetic acid/acetate buffer.

The rinsing proceeded with tap water at a temperature of 27° C. for a duration of 28 s.

Measurement of sensitivity S and square wave response SWR

The SWR values used in connection with Table I and FIG. 1 and were determined at 1 line pair per mm and 3 line pairs per mm (SWR1 and SWR3).

The determination of the SWR value for intensifying screens proceeded as described in DIN 6867, 2nd draft 1988 said intensifying screens being coated with the Gd2O2S:Tb phosphor, the composition of the coated phosphor layer of which is given in Table I.

The determination of the photographic speed S of said screens proceeded according to the International Standard method ISO/DP9236 (42N2063) Revised edition of November 1986. The values given in the tables are log values an increase by 0.30 meaning a doubling of the speed.

Stimulable phosphor screens

Measurement of sensitivity S and square wave response SWR

For the photostimulable phosphor screens coated with the BaFBr:Eu²⁺ phosphor the measurement of S and SWR was carried out with an image scanner made up with a He-Ne laser. The beam of a 10 mW red He-Ne laser is focussed to a small spot of 140 µ m (FMWH) with an optic containing a beamexpander and a collimating lens. A mirror galvanometer is used to scan this small laserspot over the entire width of a phosphor sample. During this scanning procedure the phosphor is stimulated and the emission light is captured by an array of optical fibers which are sited on one line. At the other end of the optical fibers being mounted in a circle a photomultiplier is situated.

To attenuate the stimulating light an optical filter, type BG3 from SCHOTT, is placed between the fiber and the photomultiplier. In this way only the light emitted by the phosphor is measured. The small current of the photomultiplier is first amplified with an I/V convertor and digitalised with an A/D convertor.

The measuring set up is connected with a HP 9826 computer and a HP 6944 multiprogrammer to controll the measurement. Starting the procedure an electronic shutter is closed to shut down the laser. A phosphor sample measuring 50 mm×210 mm is excited with a 85 kV X-ray source provided with an aluminum filter having a thickness of 21 mm. The radiation dose is measured with a FARMER dosemeter. Between the X-ray source and the phosphor layer a thin lead-raster containing 6 different spatial frequencies is mounted to modulate the X-ray radiation. Frequencies used are 0.025, 0.50, 0.75, 1.00, 1.50 and 3.00 line pairs per mm. After exposure the sample is put into the laser scanner. To read out one line the shutter is opened and the galvanometer is moved linearly. During the scanning procedure the emitted light is measured continuously with the A/D convertor at a sampling rate frequency of 100 kHz and stored within a memory card in the multiprogrammer. One scan thus contains 100000 pixels. Once the scan is complete the shutter is closed again and the galvanometer is put on his original position again.

The data of the scan line are transferred from the memory card in the multiprogrammer to the computer where said data are analysed. A first correction takes in account the sensitivity variation of the scan line with the distance. Therefore a calibration scan was measured previously for a phosphor sample that was exposed quite homogeneously. A second correction takes into account the amount of X-ray dose by dividing said values by the said dose amount.

The different blocks are separated and the amplitude on each spatial frequency is calculated, making use of Fourier analysis. The amplitude of the first block having a spatial frequency of 0.025 line pairs per mm is taken as the sensitivity of the stimulable phosphor screen. The other values are the results for the curve of the Square Wave Response (SWR: SWR1 referring to the response at 1 line pair per mm; SWR3 to the response at 3 line pairs per mm) which is-representative for the resolution of the screen.

Composition of the screens

In Tables I and II, the coating composition is given for the luminescent phosphor and the stimulable phosphor respectively. For each screen sample the following data referring to the composition are summarized in the respective Tables.
number of the sample (Ex. No.)
volume ratio of phosphor to binder
binder composition (CAB=cellulose acetobutyrate (30 % in 2-butanone); PS=polyethyl acrylate (30% in ethyl acetate); CAB-PS=1/1; CARIFLEX=thermoplastic rubber, trademarked product by SHELL)
amount of binder used (in g) per 100 g of phosphor
Solvent composition (EtAc=ethyl acetate; MEK=methyl ethyl ketone; EK=1/1)
thickness "d" of the phosphor layer (in μm)
packing ratio (PR), calculated as defined by the corresponding formula in EP 393 662, p. 12., given in %.

The composition contained 0.5% by weight of GAFAC RM 710 versus the total amount of pigment and was doctor blade coated onto a subbed 200 μm thick polyethylene terephthalate support and dried.

The phosphor coverage weight was about 60 mg/cm$^2$.

In the Tables values of S, SWR1 and SWR3 measured as described hereinbefore are given

TABLE I

Intensifying screens with $Gd_2O_2S$:Tb as a luminescent phosphor.

| Ex. No. | Phosphor /binder | Binder comp./amt. | Solvent comp. | S | SWR 1 | SWR 3 | d μm | PR |
|---|---|---|---|---|---|---|---|---|
| 1 | 48/52 | CABPS 17.6 | EtAcMEK | .62 | .48 | .12 | 178 | 50 |
| 2 | 59/41 | CABPS 11.1 | EtAcMEK | .68 | .51 | .14 | 154 | 56 |
| 3 | 68/32 | CABPS 7.5 | EtAcMEK | .68 | .54 | .15 | 141 | 62 |
| 4 | 63/37 | CARIFL 7.5 | EtAc | .70 | .56 | .15 | 137 | 63 |
| 5 | 71/29 | CARIFL 5.3 | EtAc | .70 | .57 | .18 | 121 | 66 |
| 6 | 87/13 | CARIFL 2.0 | EtAc | .70 | .59 | .19 | 122 | 60 |

TABLE II

Stimulable phosphor screens with BaFBr:Eu$^{2+}$ as a stimulable phosphor.

| Ex. No. | Phosphor /binder | Binder comp./amt. | Solvent comp. | S | SWR 1 | SWR 3 | d μm | PR |
|---|---|---|---|---|---|---|---|---|
| 7 | 57/43 | CABPS 17.6 | EtAcMEK | .42 | .60 | .14 | 240 | 50 |
| 8 | 67/33 | CABPS 11.1 | EtAcMEK | .46 | .68 | .19 | 207 | 54 |

TABLE II-continued

Stimulable phosphor screens with BaFBr:Eu$^{2+}$ as a stimulable phosphor.

| Ex. No. | Phosphor /binder | Binder comp./amt. | Solvent comp. | S | SWR 1 | SWR 3 | d μm | PR |
|---|---|---|---|---|---|---|---|---|
| 9 | 75/25 | CABPS 7.5 | EtAcMEK | .47 | .70 | .21 | 193 | 58 |
| 10 | 71/29 | CARIFL 7.5 | EtAc | .54 | .69 | .19 | 225 | 60 |
| 11 | 78/22 | CARIFL 5.3 | EtAc | .49 | .72 | .22 | 176 | 62 |
| 12 | 90/10 | CARIFL 2.0 | EtAc | .62 | .73 | .21 | 210 | 60 |

These results should be interpreted in relation to the physical properties of the screens, summarized in Table III. Terms like "elasticity/brittleness" and "adhesion" have been measured as given hereinbefore and should be interpreted as such.

TABLE III

Physical properties of the screens given in Tables I and II.

| Ex. No. | Elasticity/Brittleness | Adhesion |
|---|---|---|
| 1/7 | A | A |
| 2/8 | A | B |
| 3/9 | B | C |
| 4/10 | A | A |
| 5/11 | A | B |
| 6/12 | A | B |

An increased ratio of pigment to binder results in an increase in sensitivity and sharpness as can be seen from Tables I and II.

Only with CARIFLEX-thermoplastic rubbers it is possible to reach a high-er ratio value of pigment to binder with acceptable physical properties. For the highest pigment/ binder ratio value of screens with other binders than CARIFLEX thermoplastic binders the physical properties of the screens are already inferior (more brittleness, bad adhesion properties), whereas with CARIFLEX thermoplastic binder it is possible to enhance further the said ratio, which results in an enhanced sensitivity and sharpness, without remarkably offering the good physical properties.

We claim:

1. Method of producing a luminescent article comprising a self-supporting or a supported layer of phosphor particles dispersed in a binding medium and a protective coating thereover wherein said binding medium consists essentially of one or more rubbery and/or elastomeric polymers, in that the ratio by volume of phosphor to binding medium is at least 70:30 and at most 92:8 and in that the packing ratio is less than 67%, and wherein said luminescent article is prepared by the steps of dispersing phosphor particles in a binding medium consisting essentially of said rubbery and/ or elastomeric polymers, coating said dispersed phosphor particles so as to form a phosphor layer without compressing the said dried phosphor layer and coating a protective coating thereover.

2. Method of producing a luminescent article according to claim 1, wherein the ratio by volume of phosphor to binder is at least 85:15.

3. Method of producing a luminescent article according to claim 1, wherein said rubbery and/or elastomeric polymers are selected from the group consisting of natural rubbers and synthetic rubbers.

4. Method of producing a luminescent article according to claim 1, wherein said rubbery and/or elastomeric polymers are selected from the group consisting of thermoplastic elastomers and thermoplastic rubbers.

5. Method of producing a luminescent article according to claim 1, wherein said thermoplastic elastomers and/or thermoplastic rubbers are thermoplastic block-copolymers with elastomeric properties.

6. Method of producing a luminescent article according to claim 5, wherein said thermoplastic block-copolymers are selected from styrene-butadiene, isoprene and butadiene or a mixture thereof.

7. Method of producing a luminescent article according to claim 1, wherein said phosphor layers have a thickness in the range of 100 to 300 µm.

8. Method for producing a luminescent article according to claim 1, wherein an average grain size of said phosphor particles is in the range of 2 to 20 µm.

9. Method of producing a luminescent article according to claim 1, wherein said self-supporting or supported phosphor layers is present on a fluorescent light absorbing antihalation layer or light-reflecting layer.

10. Method of producing a luminescent article according to claim 1, wherein said luminescent article is an X-ray intensifying screen comprising at least one luminescent phosphor or is a storage panel comprising at least one stimulable phosphor.

11. Method of producing a luminescent article according to claim 1, wherein said protective coating is electron radiation cured and wherein the edges of the screen are edge-reinforced with a moisture-hardened polymer composition.

12. Method of producing a luminescent article according to claim 1, wherein said phosphor layer comprises at least one antioxidant.

* * * * *